(12) United States Patent
Matsuo

(10) Patent No.: US 10,888,308 B2
(45) Date of Patent: Jan. 12, 2021

(54) TISSUE COLLECTOR

(71) Applicant: OLYMPUS CORPORATION, Tokyo (JP)

(72) Inventor: Nobuko Matsuo, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 184 days.

(21) Appl. No.: 16/142,520

(22) Filed: Sep. 26, 2018

(65) Prior Publication Data

US 2019/0021714 A1 Jan. 24, 2019

Related U.S. Application Data

(63) Continuation of application No. PCT/JP2016/060324, filed on Mar. 30, 2016.

(51) Int. Cl.
| | |
|---|---|
| *A61B 17/00* | (2006.01) |
| *A61B 10/02* | (2006.01) |
| *A61B 10/04* | (2006.01) |
| *A61B 1/00* | (2006.01) |
| *A61B 1/313* | (2006.01) |

(52) U.S. Cl.
CPC ...... *A61B 17/00234* (2013.01); *A61B 1/0014* (2013.01); *A61B 1/313* (2013.01); *A61B 10/02* (2013.01); *A61B 10/04* (2013.01); *A61B 2017/00287* (2013.01); *A61B 2017/00296* (2013.01); *A61B 2017/00367* (2013.01); *A61B 2017/00862* (2013.01)

(58) Field of Classification Search
CPC ......... A61B 1/313; A61B 10/02; A61B 10/04; A61B 17/00234; A61B 2017/00287; A61B 2017/00296; A61B 2017/00367; A61B 2017/00862; A61B 17/22

See application file for complete search history.

(56) References Cited

U.S. PATENT DOCUMENTS

| 8,425,533 B2 | 4/2013 | Parihar et al. |
| 2002/0156344 A1 | 10/2002 | Pasricha et al. |
| 2010/0152612 A1* | 6/2010 | Headley, Jr. ........... A61B 10/04 600/566 |

(Continued)

FOREIGN PATENT DOCUMENTS

| EP | 2474270 A2 | 7/2012 |
| JP | 2002-336263 A | 11/2002 |

(Continued)

OTHER PUBLICATIONS

International Search Report dated Jul. 5, 2016 issued in PCT/JP2016/060324.

*Primary Examiner* — George J Ulsh
(74) *Attorney, Agent, or Firm* — Scully, Scott, Murphy & Presser, P.C.

(57) ABSTRACT

A tissue collector includes: an elongated sheath; a bag; a wire bending portion; and an extending portion which is arranged at the distal end portion of the sheath so as to protrude forward from the distal end portion along the longitudinal axis and enter an inside of the bag. The extending portion intersects with the opening surface that is defined by an opening end of the opening portion. The extending portion is configured to be capable of extending inside the bag from an opening surface toward the bottom portion.

13 Claims, 11 Drawing Sheets

(56) References Cited

U.S. PATENT DOCUMENTS

| | | | |
|---|---|---|---|
| 2011/0184431 A1 | 7/2011 | Parihar et al. | |
| 2014/0180303 A1 | 6/2014 | Duncan et al. | |
| 2014/0371760 A1* | 12/2014 | Menn | A61B 17/29 606/114 |
| 2016/0278757 A1* | 9/2016 | Piskun | A61B 1/32 |
| 2017/0333061 A1* | 11/2017 | Atwell | A61B 17/221 |
| 2018/0146958 A1* | 5/2018 | Mikkaichi | A61B 10/0096 |

FOREIGN PATENT DOCUMENTS

| | | |
|---|---|---|
| JP | 2005-021620 A | 1/2005 |
| JP | 2012-143538 A | 8/2012 |

\* cited by examiner

TISSUE COLLECTOR

This application is a continuation application based on PCT/JP2016/060324, filed on Mar. 30, 2016. The content of the PCT Application is incorporated herein by reference.

TECHNICAL FIELD

The present invention relates to a tissue collector.

BACKGROUND ART

Conventionally, a treatment for collecting a tissue is performed, using a treatment instrument inserted in a channel of a flexible endoscope. When the tissue to be collected is from a lesion such as a tumor or the like, the tissue is removed with an endoscope while grasping the resected tissue by a forceps or the like, and the tissue is accommodated by a collector that is attached to the endoscope. As such a collector, for example, a collector disclosed in Japanese Unexamined Patent Application, First Publication No. 2005-21620 is known.

SUMMARY OF INVENTION

According to one aspect of the present invention, the tissue collector includes: an elongated sheath which has a proximal end portion and a distal end portion and which extends in a direction of a longitudinal axis; a bag which has an opening portion and a bottom portion, which is arranged at the distal end portion, and which is capable of expanding and contracting; a wire bending portion which protrudes forward from the distal end portion and which is configured to expand the opening portion by moving forward from the distal end portion; and an extending portion which is arranged at the distal end portion of the sheath so as to protrude forward from the distal end portion along the longitudinal axis and enter an inside of the bag. The extending portion intersects with the opening surface that is defined by an opening end of the opening portion and is configured to be capable of extending inside the bag from an opening surface toward the bottom portion.

The tissue collector of the above aspect further may include an elastic wire which extends along the opening end and which holds the opening end annularly. The tissue collector may have a pair of tubular portions that are spaced from each other as going forward from the distal end portion and that internally hold the elastic wire such that the elastic wire is capable of being advanced and retracted.

The wire bending portion may include an elastic wire which has a ring shape that extends from the distal end portion along the opening end and that returns to the distal end portion again.

In the direction of the longitudinal axis, the distal end of the extending portion is positioned forward the wire bending portion in a state where the bag is raised.

The bag may have a fold line which extends from the opening portion toward the bottom portion such that the bag is folded and unfolded by the extending portion.

The tissue collector of the above aspect further may include: a raising wire which has one end that is fixed to the opening end and which extends to the proximal end portion along the sheath; and an operation portion which is arranged at a proximal end portion of the sheath and which is connected to the raising wire.

The tissue collector of the above aspect further may include a connecting portion that connects the sheath to an insertion portion of an endoscope such that the sheath extends along a longitudinal direction of the insertion portion. The connecting portion may hold the sheath such that the sheath is capable of being advanced and retracted along the longitudinal axis of the sheath. The connecting portion may hold the sheath such that the sheath is rotatable about the longitudinal axis of the sheath.

The bag may be a conical shape, and the bottom portion may be a tip of the conical shape. The extending portion may be configured to support an opening of the bag by holding a portion of the bag contacting to the extending portion when the bag is raised with respect to the sheath, and may be arranged so as to be capable of forming a space that is capable of accommodating a tissue into the bag.

The tissue collector further may include a raising operation portion which is provided at the proximal end portion of the sheath and is capable of raising the opening portion toward the proximal end portion of the sheath; and a thread which is connected to the raising operation portion and the opening end of the opening portion.

A tissue collector system of the present invention includes the tissue collector of the above aspect, and an endoscope which is attached along the longitudinal axis on an outer peripheral surface of the sheath and which includes an observation surface that observes a target and that is provided in a distal end surface of the endoscope.

The tissue collector system further may include a raising operation portion which tows a thread fixed to the opening end of the opening portion toward the proximal end portion side of the sheath such that the observation surface of the endoscope and the opening surface of the opening portion face each other.

DESCRIPTION OF EMBODIMENTS

First Embodiment

Figure 1:
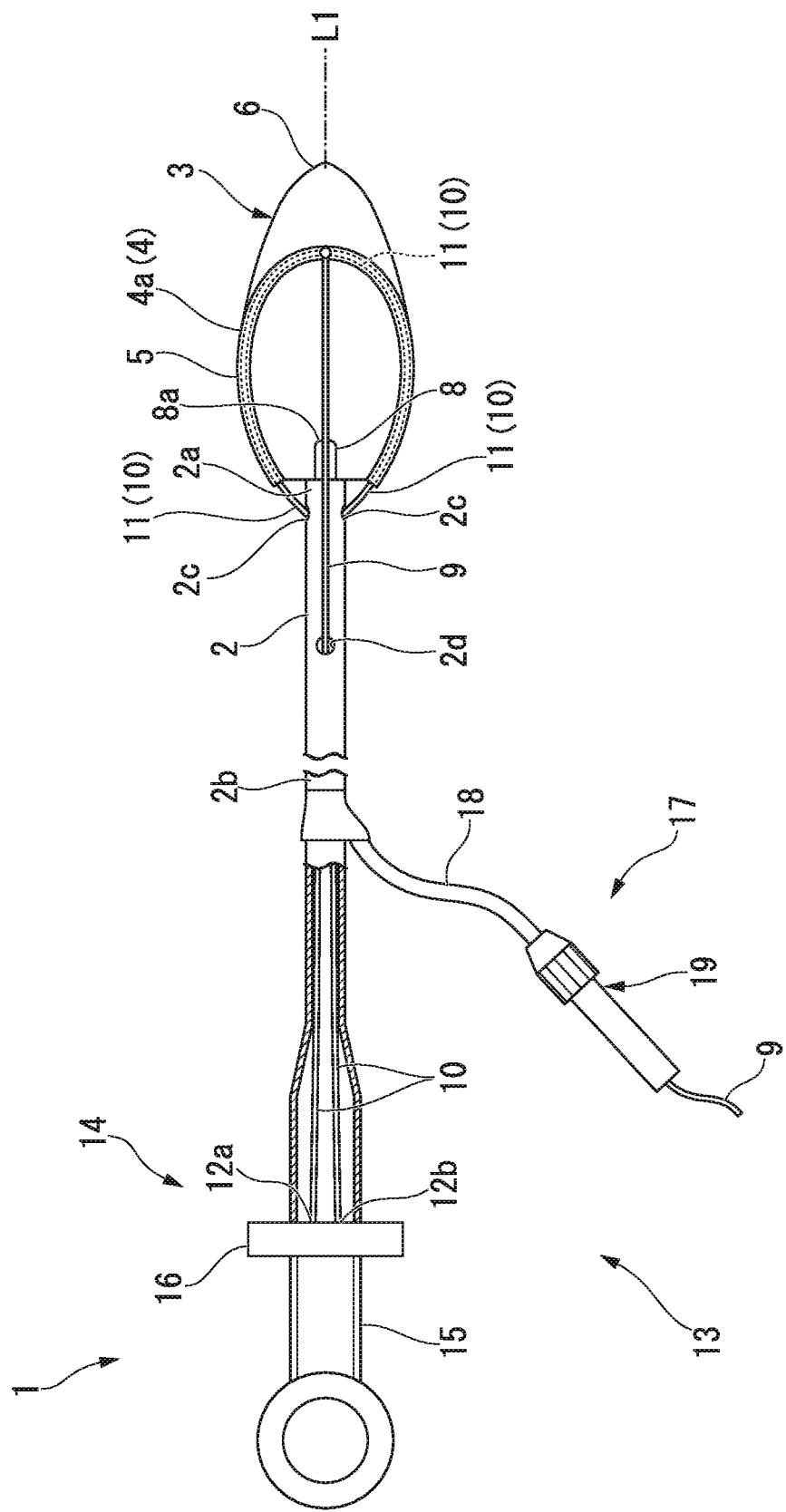
FIG. 1 is an overall view showing a tissue collector of a first embodiment of the present invention.
Figure 2:
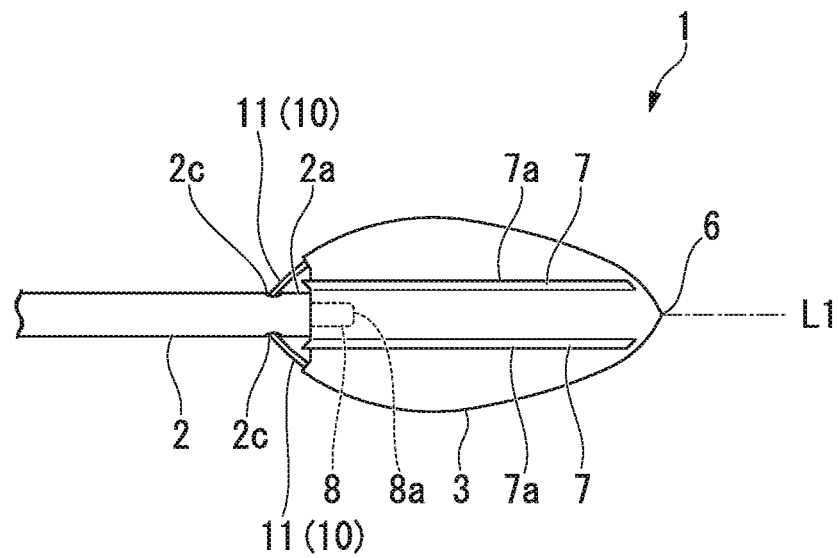
FIG. 2 is a rear view of a vicinity of a distal end of the tissue collector.
Figure 3:
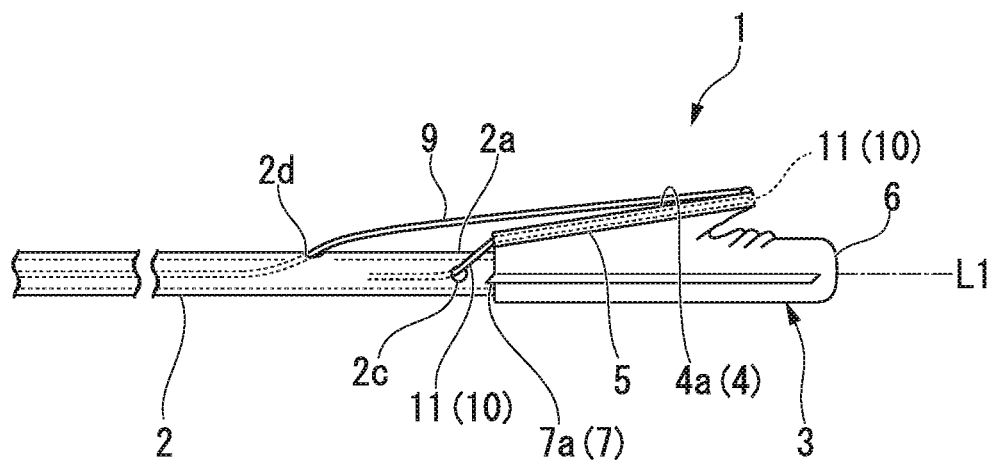
FIG. 3 is a side view showing a state in which a bag of the tissue collector is not lifted.
Figure 4:
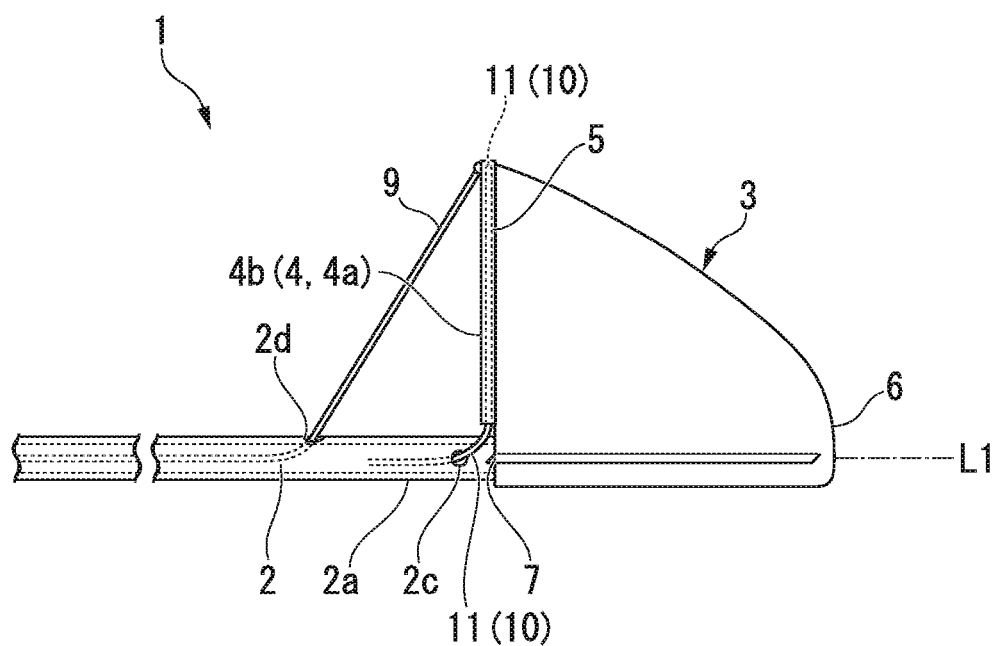
FIG. 4 is a side view showing a state in which the bag is lifted.
Figure 5:
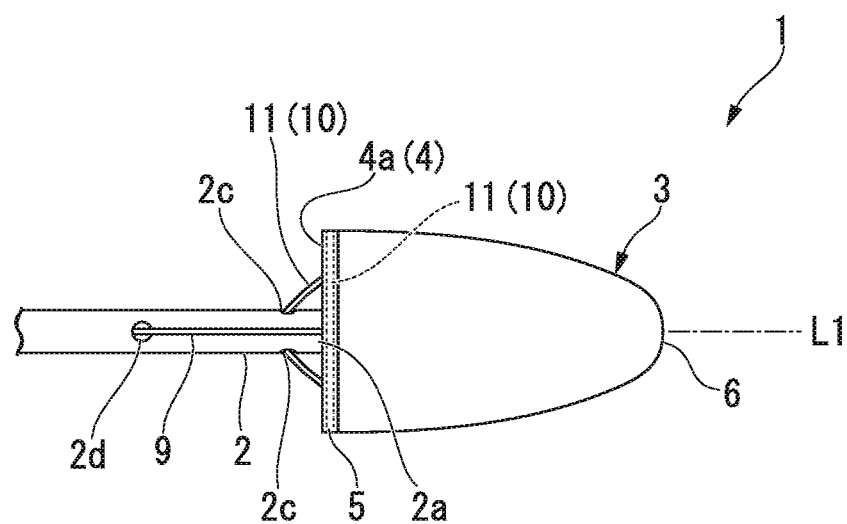
FIG. 5 is a plan view showing a state in which the bag is lifted.
Figure 6:
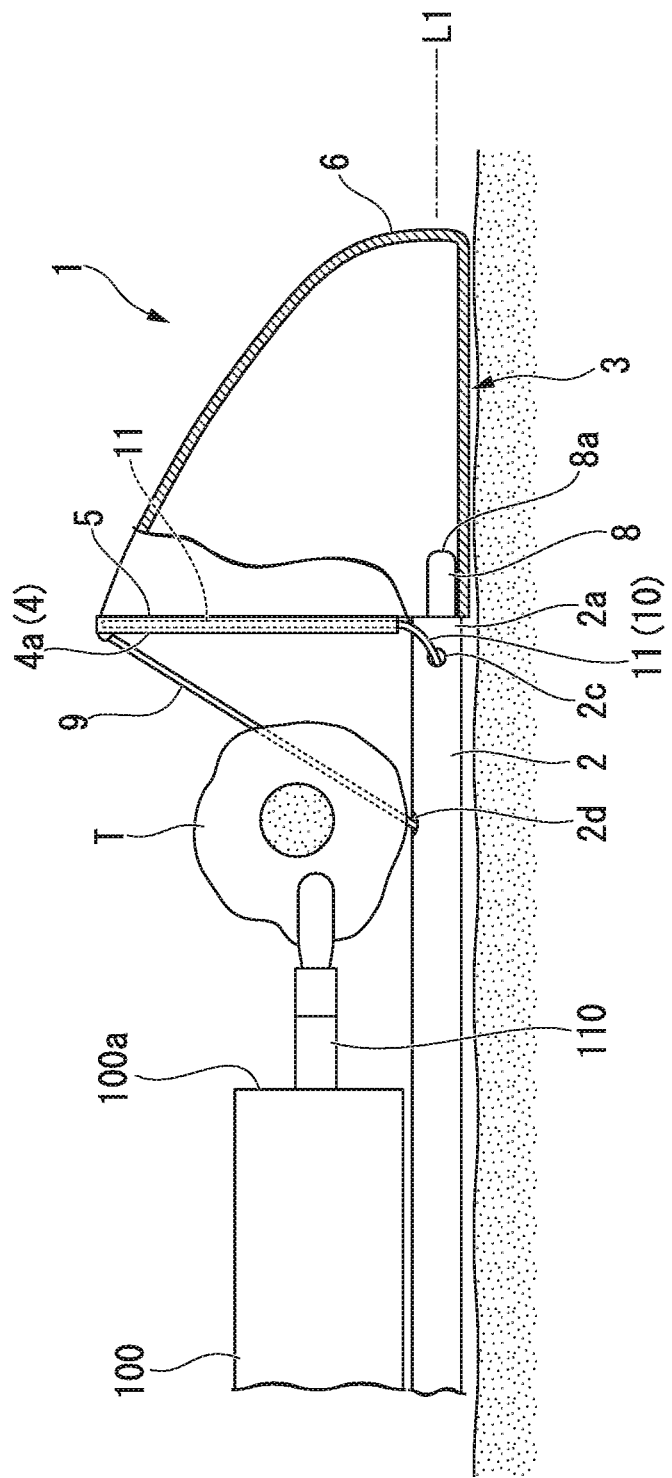
FIG. 6 is a diagram for explaining the operation of the tissue collector.

A first embodiment of the present invention will be described. FIG. 1 is an overall view showing a tissue collector of the present embodiment. FIG. 2 is a rear view of a vicinity of a distal end of the tissue collector. FIG. 3 is a side view showing a state in which a bag of the tissue collector is not raised. FIG. 4 is a side view showing a state in which the bag is raised. FIG. 5 is a plan view showing a state in which the bag is raised. FIG. 6 is a diagram for explaining the operation of the tissue collector.

As shown in FIG. 1 and FIG. 2, the tissue collector 1 (hereinafter simply referred to as "collector 1") of the present embodiment includes a longitudinal inner sheath 2, a bag 3, an extending portion 8, a thread 9, a first wire 10, and an operation portion 13.

The inner sheath 2 has a distal end portion 2a and a proximal end portion 2b and is an elongated tubular member extending in a direction of a longitudinal axis L1. The bag 3 is provided in the distal end portion 2a of the inner sheath 2. An operation portion 13 is provided in the proximal end portion 2b of the inner sheath 2. A pair of first holes 2c for extending the first wire 10 are formed on both side surfaces of the distal end portion 2a of the inner sheath 2. A second hole 2d for extending the thread 9 from the inside of the inner sheath 2 is formed at a position apart from the distal end portion 2a of the inner sheath 2 by a predetermined distance toward the proximal end side.

The bag 3 is formed of a thin film which is capable of isolating a resected tissue and liquid. The material of the bag 3 is a flexible material having biological compatibility. For example, the bag 3 is formed of urethane or the like.

As shown in FIG. 2 and FIG. 3, the bag 3 has an opening portion 4, a bottom portion 6, and a fold line 7. The opening portion 4 of the bag 3 protrudes forward from the distal end portion 2a of the inner sheath 2. The bottom portion 6 of the bag 3 is positioned further forward than the distal end portion 2a of the inner sheath 2.

The opening portion 4 is connected to the distal end portion 2a of the inner sheath 2. The opening portion 4 is connected to the thread 9 at a position farthest from the distal end 2a of the inner sheath 2.

A direction of the opening portion 4 of the bag 3 varies according to a towing operation by the thread 9. That is, as the bag 3 is towed by the thread 9, the direction of the opening portion 4 of the bag 3 changes between the direction of the longitudinal axis L1 of the inner sheath 2 and a direction orthogonal to the longitudinal axis L1.

The opening portion 4 of the bag 3 has a tubular insertion passage 5 such that the first wire 10 defining a shape of the opening end 4a of the opening portion 4 can be inserted.

The bottom portion 6 of the bag 3 is a linear shape parallel to the opening surface 4b that is defined by the opening end 4a of the opening portion 4. In a state where the bag 3 is most suitably opened, the bottom portion 6 of the bag 3 extends along a straight line intersecting the longitudinal axis L of the inner sheath 2.

As shown in FIG. 2 to FIG. 4, the fold line 7 extends from the opening portion 4 toward the bottom portion 6. Two folds 7 are arranged on both sides of the bag 3 with the extended portion 8 therebetween. The fold line 7 has a ridge line portion 7a that is formed such that part of the bag 3 protrudes toward an outside of the bag 3 and part of the bag 3 including the ridge line portion 7a is thermally welded, thereby the ridge line portion 7a is formed. The fold line 7 is harder than the other portions of the bag 3 and the bag 3 is supported by maintaining a long linear shape in a direction in which the ridge line portion 7a extends such that the bag 3 is easily opened in a bag shape. The position and the number of the fold line 7 are not particularly limited as long as the fold line 7 extends from the opening portion 4 toward the bottom portion 6. For example, as shown in FIG. 2 to FIG. 4, a fold line (not shown) may be formed at another place in addition to the fold line 7 formed in a vicinity of the extending portion 8.

The extending portion 8 is arranged at the distal end portion 2a of the inner sheath 2 so as to be brought into contact with a vicinity of the opening portion 4 of the bag 3. The extending portion 8 further extends forward from the distal end portion 2a of the inner sheath 2 along the longitudinal axis L1 of the inner sheath 2.

In the present embodiment, the distal end 8a of the extending portion 8 contacts the bag 3 in a state where the bag 3 is raised by a raising operation portion 17 (see FIG. 1) described later. In a state where the bag 3 is lifted, the extending portion 8 extends from the opening portion 4 of the bag 3 toward the bottom portion 6. The length of the extending portion 8 in the longitudinal axis L1 direction of the inner sheath 2 is equal to or longer than the length at which the distal end 8a of the extending portion 8 is capable of coming into contact with the bag 3 or is equal to or less than the length from the opening portion 4 of the bag 3 that is towed to the bottom portion 6. In the longitudinal axis L1 direction of the inner sheath 2, the distal end 8a of the extending portion 8 is positioned further forward than the wire bending portion 11 that is a distal end of the first wire 10.

As shown in FIG. 1 and FIG. 2, the thread 9 is connected to a raising operation unit 17 (described later) of the operation unit 13 and is connected to the opening portion 4 of the bag 3. The thread 9 is inserted through a second hole 2d that is formed in the inner sheath 2. In the present embodiment, the thread 9 extends from the second hole 2d of the inner sheath 2 to the outside of the inner sheath 2 and is fixed to the opening portion 4 of the bag 3.

The first wire 10 is an elastic wire that is elastically deformable. The first wire 10 has a wire bending portion 11 and both ends 12a and 12b.

The wire bending portion 11 is formed by folding back an intermediate portion in the longitudinal direction of the first wire 10. In a state where no external force is applied, the wire bending portion 11 is annular, for example, which is wider than a diameter of the inner sheath 2. That is, the wire bending portion 11 bulges outwardly in a radial direction of the inner sheath 2 such that the pair of wires gradually separate symmetrically with respect to the longitudinal axis L1 of the inner sheath 2 from a proximal end portion to an intermediate portion of the wire bending portion 11. The wire bending portion 11 gradually narrows inward in the radial direction of the inner sheath 2 as the wire bending portion 11 goes from the intermediate portion to a distal end portion of the portion 11.

A region from the proximal end portion to the intermediate portion of the wire bending portion 11 is a pair of opening and closing members for expanding the opening portion 4 in the present embodiment.

The wire bending portion 11 is inserted through the opening portion 4 of the bag 3. In the present embodiment, the wire bending portion 11 extends along the opening end 4a by being inserted into the insertion passage 5 formed in the opening portion 4. The wire bending portion 11 annularly holds the opening end 4a of the opening portion 4. The wire bending portion 11 defines a shape of the opening portion 4 according to a protrusion amount from the distal end portion 2a of the inner sheath 2 in a forward direction. That is, in a state where no external force is applied to the wire bending portion 11, when the wire bending portion 11 moves forward from the distal end portion 2a of the inner sheath 2, the wire bending portion 11 moves with respect to the longitudinal axis L1 of the inner sheath 2 so as to spread symmetrically away from the longitudinal axis L1 and the opening portion 4 is expanded, thereby the opening portion 4 is held such that the opening portion 4 is annular. When the first wire 10 is located on the proximal end side such that the wire bending portion 11 is positioned in the vicinity of the distal end portion 2a of the inner sheath 2, the wire bending portion 11 holds the opening portion 4 such that the opening portion 4 is reduced in diameter.

In a region forward of the distal end portion 2a of the inner sheath 2, the first wire 10 has a ring shape that extends from the distal end portion 2a of the inner sheath 2 along the opening end 4a of the opening portion 4 of the bag 3 and reaches the distal end portion 2a of the inner sheath 2 again.

Both ends 12a, 12b of the first wire 10 are positioned at the base end portion 2b of the inner sheath 2. Both ends 12a, 12b of the first wire 10 are connected to the slider 16 of the operation portion 13.

In the first wire 10, a portion between the wire bending portion 11 and both ends 12a, 12b is inserted into the inner sheath 2.

The first wire 10 is made of a shape memory alloy such as elastically deformable nickel titanium or the like. In the first wire 10, the wire bending portion 11 is given in advance a curved shape for defining the shape of the opening portion 4. The wire bending portion 11 extends along the opening end 4a of the opening portion 4 by being inserted into the insertion passage 5 of the opening portion 4. The first wire 10 exposed from the insertion path 5 is inserted into a pair of first holes 2c that are formed to face a side surface of the inner sheath 2.

As shown in FIG. 1, the operation portion 13 is arranged at the proximal end portion 2b of the inner sheath 2. The operation portion 13 includes an opening-closing operation portion 14 for opening and closing the opening portion 4 of the bag 3, and the raising operation portion 17 for raising the bag 3. The opening-closing operation portion 14 includes an operating portion main body 15 and a slider 16.

The slider 16 is connected to the operating portion main body 15 so as to be capable of sliding with respect to the operating portion main body 15. The slider 16 is fixed to both ends 12a, 12b of the first wire 10.

When the slider 16 is moved forward with respect to the operating portion main body 15, the first wire 10 moves forward and the first wire 10 protrudes forward from the distal end portion 2a of the inner sheath 2. In the first wire 10, the wire bending portion 11 deforms the opening portion 4 such that the opening portion 4 of the bag 3 opens annularly. By a forward and backward movement of the first wire 10 using the slider 16, an entrance for inserting the tissue into the inside of the bag 3 is formed in the bag 3.

The raising operation portion 17 includes a branching tube 18 that has one end connected to the inner sheath 2 and a thread fixing member 19 that is arranged at the other end of the branching tube 18. The thread fixing member 19 switches between a state where a position of the thread 9 is fixed to the branching tube 18 and a state where the thread 9 is freely movable forward and backward relative to the branching tube 18. When the thread 9 is fixed to the thread fixing member 19 in a state where the thread 9 is towed, the thread 9 is maintained in a state where the opening portion 4 of the bag 3 is raised. When the thread fixing member 9 to the thread fixture 19 is released, the opening portion 4 is restored to a state of protruding toward the distal side in the longitudinal axis L1 direction of the inner sheath 2.

The thread 9 is capable of fixing to the thread fixing member 19 at an arbitrary position. Therefore, a raising angle of the opening portion 4 of the bag 3 with respect to the longitudinal axis L1 of the inner sheath 2 can be set to an arbitrary angle by using the raising operation portion 17 that includes the thread fixing member 19 of the present embodiment.

The collector 1 of the present embodiment will be described. FIG. 6 is a diagram for explaining the operation of the tissue collector.

As shown in FIG. 6, the collector 1 of the present embodiment is inserted into the body together with the endoscope 100.

First, the opening portion 4 of the bag 3 is opened (see FIG. 3) by moving the first wire 10 forward using the opening-closing operation portion 14 (see FIG. 1). At this time, since the fold line 7 is formed in the bag 3, the portion between the opening portion 4 and the bottom portion 6 of the bag 3 is opened together with the opening portion 4 by a force in which the first wire 10 opens the opening portion 4.

When the thread 9 is towed to the proximal end side by using the raising operation portion 17 in a state where the opening portion 4 of the bag 3 protrudes in the longitudinal axis L1 direction of the inner sheath 2, the thread 9 raises the opening portion 4. Then, a positional relationship between the bag 3 and the extending portion 8 changes such that the extending portion 8 intersects with the opening surface 4b defined by the opening end 4a of the opening portion 4 and directs toward the bottom portion 6 of the bag 3 (see FIGS. 4 and 5). In the process of raising the bag 3, the extending portion 8 presses the bag 3 such that the portion of the bag 3 contacting the extending portion 8 is not raised. As a result, even when the opening between the opening portion 4 and the bottom 6 of the bag 3 is not sufficiently opened in the operation using the opening-closing operation portion 14, a space is formed in the bag 3 that can accommodate part of the tissue.

As shown in FIG. 6, the raising operation portion 17 tows a thread 9 fixed to the opening end 4b of the opening portion 4 toward the proximal end portion side of the sheath 2 such that an observation surface 100a of the endoscope 100 and the opening surface 4b of the opening portion 4 face each other. The observation surface 100a is provided at the distal end of the endoscope 10X). In a state where the bag 3 is raised, the tissue T can be inserted into the bag 3 through the opening portion 4 using the endoscopic grasping forceps 110 or the like. In the bag 3, since the space as a trigger for pushing out the bag 3 already has been generated by the wire bending portion 11 and the extending portion 8 of the first wire 10, in the process of inserting the tissue into the bag 3, the bag 3 easily spreads, and even if the tissue is a large volume, it can be easily accommodated in the bag 3.

After insertion of the tissue T into the bag 3, the slider 16 is moved toward the proximal end side with respect to the operating portion main body 15 (see FIG. 1). Then, both ends 12a, 12b of the first wire 10 move further toward the proximal end side than the proximal end portion 2b with respect to the inner sheath 2. Since the first wire 10 is inserted into the insertion passage 5 of the opening portion 4, when the wire bending portion 11 is towed toward the proximal end side, the opening portion 4 is reduced in diameter and the bag 3 is closed. In the state where the bag 3 closed, the collector 1 is pulled out of the body, thereby the tissue can be taken out of the body.

As described above, according to the collector 1 of the present embodiment, when the opening portion 4 of the bag 3 is opened by using the first wire 10, even when the open of a part of the bag 3 is insufficient, the extension portion 8 helps the open of the bag 3, thereby a space that is a sufficient size can be formed in the bag 3 as a trigger for accommodating the tissue after raising the bag 3. As a result, in the collector 1 of the present embodiment, it is easy to open the bag 3.

Since the first wire 10 of the collector 1 of the present embodiment is a ring shape along the open end 4a of the opening portion 4 of the bag 3 in the region forward of the distal end portion 2a of the inner sheath 2, it is possible to support the bag 3 using the first wire 10 such that the portion 4 is a neat annular shape.

In the present embodiment, when the bag 3 is in the raised state, since the distal end 8a of the extending portion 8 is positioned ahead of the wire bending portion 11, according to the collector 1 of the present embodiment, a space for accommodating the tissue can be formed widely in the bag 3 in the process of raising the bag 3

Since the fold line 7 is formed in the bag 3, the bag 3 is easily opened such that the ridge line of the fold line 7 becomes linear in the process of raising the bag 3 in the folded state. In the present embodiment, since the fold line 7 extends from the opening portion 4 of the bag 3 toward the bottom portion 6, a space that is capable of accommodating the tissue is formed in the entire area from the opening portion 4 of the bag 3 to the bottom portion 6.

In the present embodiment, the fold line 7 is formed in a rib shape perpendicular to the outer peripheral surface of the bag 3. Thus, the bag 3 can be reinforced by the fold line 7. Consequently, it is possible to prevent the suitably opened bag 3 from unintentionally being folded again.

In the present embodiment, the tissue can be accommodated in the bag 3 in either of the state in which the bag 3 is raised and the state in which the bag 3 is not raised. Therefore, the opening portion 4 can be oriented in a direction having a positional relationship with the instrument such as the endoscope grasping forceps for housing the tissue in the bag 3 such that it is easy to put the tissue in the bag 3.

Modified Example 1-1

Figure 7A:
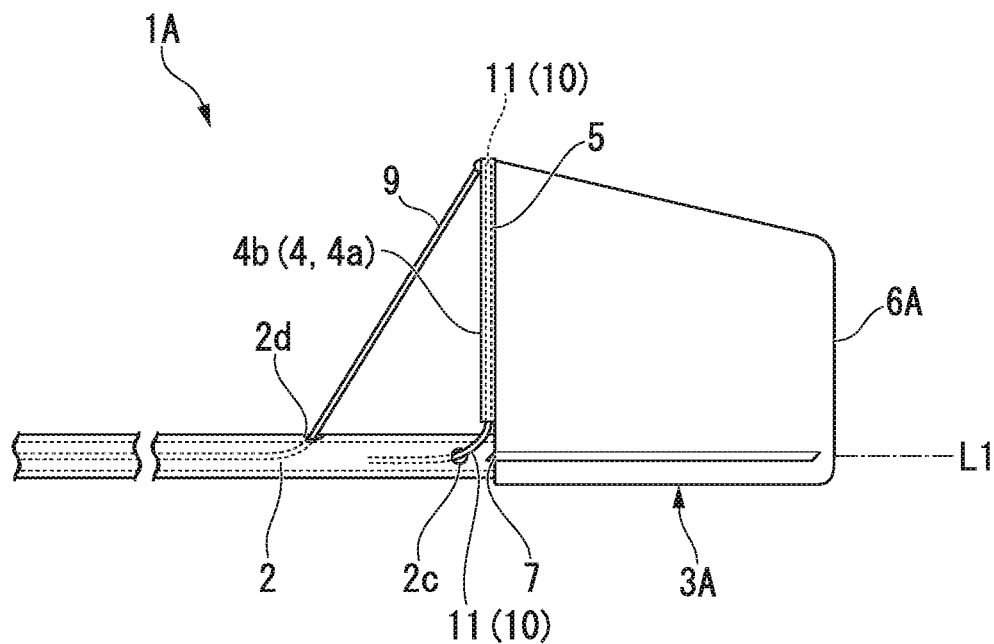
FIG. 7A is a view showing a modified example of the bag of the tissue collector of the present embodiment and is a side view.
Figure 7B:
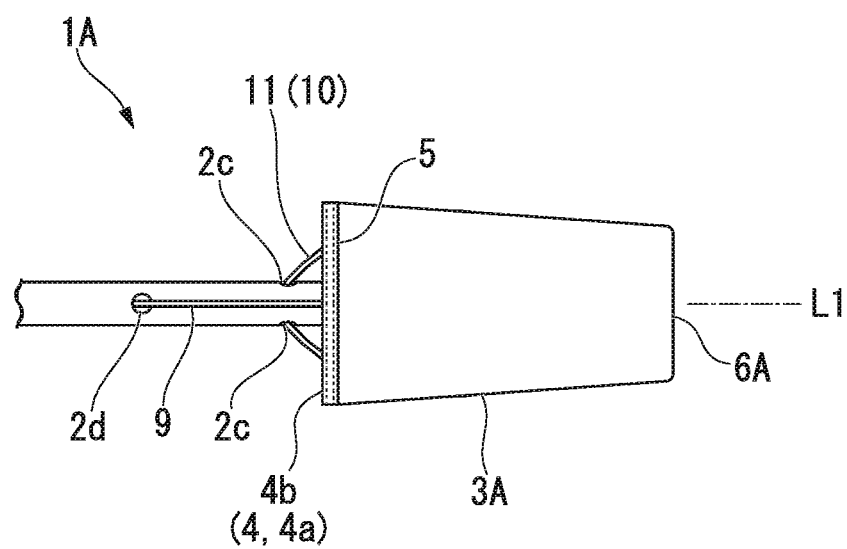
FIG. 7B is a view showing a modified example of the bag of the tissue collector of the present embodiment and is a plan view.

A modified example of the above embodiment will now be described. FIG. 7A is a view showing the bag of the tissue collector of this modified example and a side view. FIG. 7B is a view showing the bag of the tissue collector of this modified example and a plan view.

As shown in FIG. 7, the collector 1 A of this modified example has a bag 3A having a shape different from that of the bag 3 disclosed in the above embodiment.

The bottom portion 6b of the bag 3A in the present modified example has a planar shape parallel to the opening surface 4b defined by the opening end 4a of the opening portion 4. That is, the bag 3A in this modified example is substantially in the shape of a truncated cone when the bag 3A is most suitably opened in a state where the bag 3A is raised.

In this modified example, in a state in which the bag 3A is raised, the extending portion 8 crosses the opening surface 4b defined by the opening end 4a of the opening portion 4 of the bag 3A and extends toward the bottom portion 6A.

[Modification 1-2]

Figure 8A:
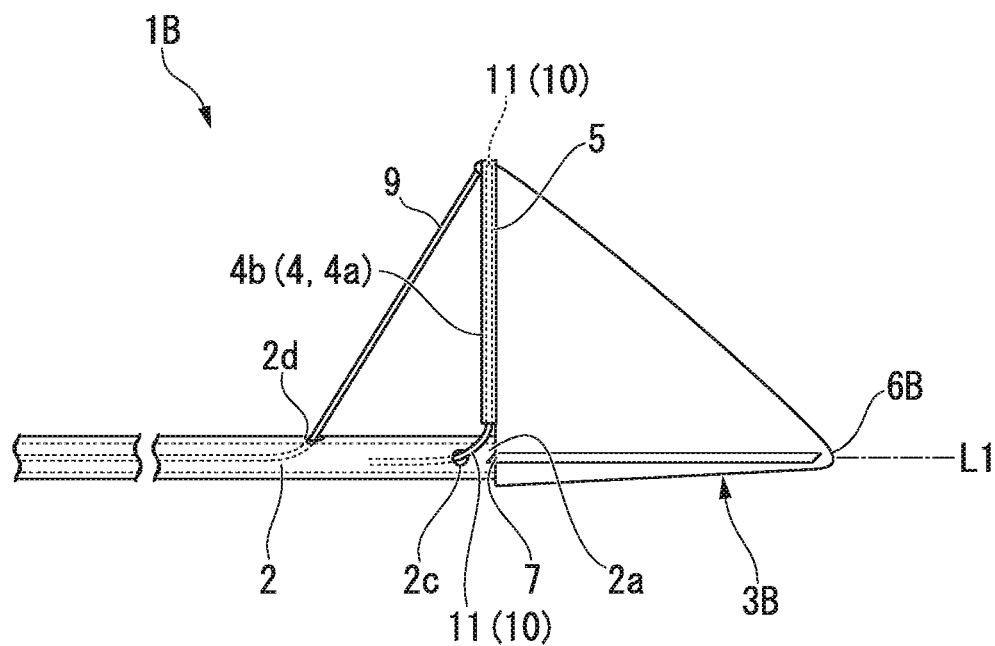
FIG. 8A is a view showing a modified example of the bag of the tissue collector of the present embodiment and is a side view.
Figure 8B:
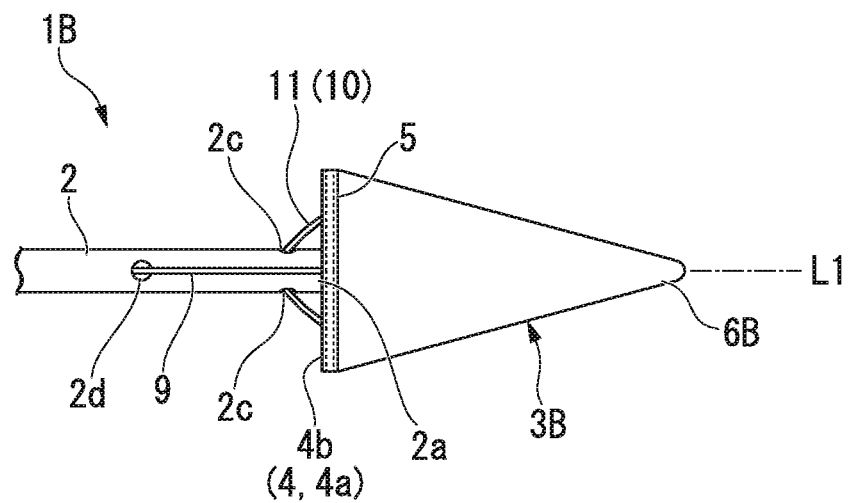
FIG. 8B is a view showing a modified example of the bag of the tissue collector of the present embodiment and is a plan view.

Another modified example of the above embodiment will be described. FIG. 8A and FIG. 8B are a side view showing the bag of the tissue collector of the present modification, FIG. 8A being a side view, and FIG. 8B being a plan view.

As shown in FIG. 8, the collector 1B of this modified example has a bag 3B having a shape different from that of the bag 3 disclosed in the above embodiment.

In other words, the bag 3B in this modified example has a substantially conical shape when the bag 3B is most suitably deployed in a raised state. The bottom portion 6B of the bag 3B in this modified example is a tip of the conical shape.

In this modified example, in a state where the bag 3B is raised, the extending portion 8 crosses the opening surface 4b defined by the opening end 4a of the opening portion 4 of the bag 3B and extends toward the bottom portion 6.

Second Embodiment

Figure 9:
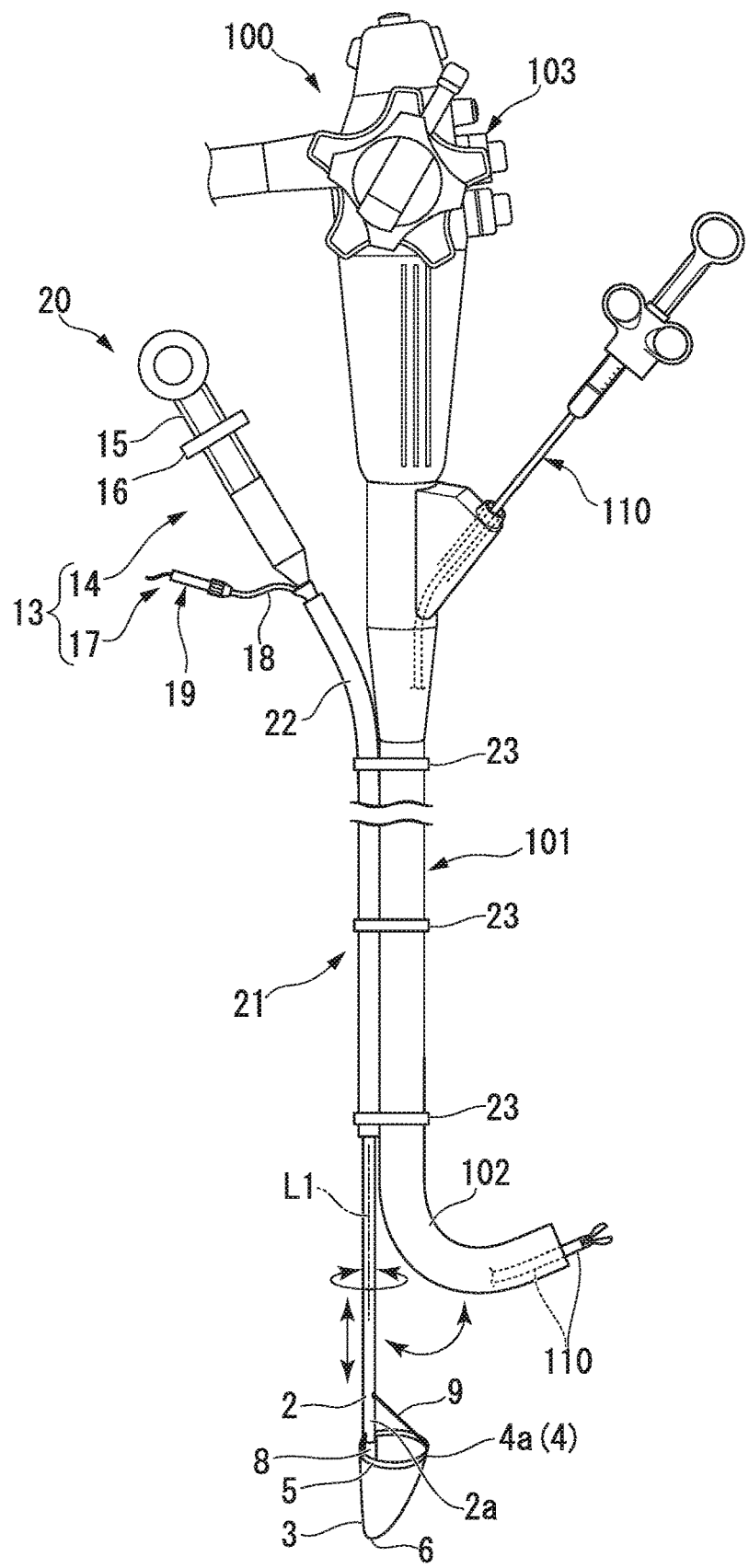
FIG. 9 is an overall view showing a state where the tissue collector of a second embodiment is attached to the endoscope.

A second embodiment of the present invention will be described. FIG. 9 is an overall view showing a state where the tissue collector of the present embodiment is attached to the endoscope.

As shown in FIG. 9, the collector 20 of the present embodiment can be attached to the insertion portion 101 of the endoscope 100. That is, the collector 1 has a connection portion 21 for connecting the inner sheath 2 to the insertion portion 101 of the endoscope 100.

The connecting portion 21 includes an outer sheath 22 that holds the inner sheath 2 in a state where the inner sheath 2 is inserted therein, and a fixing member 23 that has a ring shape and fixes the outer sheath 22 to the insertion portion 101 of the endoscope 100.

In the present embodiment, the inner sheath 2 inserted through the outer sheath 22 is freely advanced and retracted in the longitudinal axis L1 direction of the inner sheath 2 and is rotatable about the longitudinal axis L1 of the inner sheath 2.

The fixing member 23 fixes the outer sheath 22 to the insertion portion 101 at a plurality of positions in the longitudinal direction of the insertion portion 101 of the endoscope 100. For example, in the insertion portion 101 of the endoscope 100, the fixing member 23 is attached to the proximal side of the active bent portion 102 (the side close to the operation portion 103 of the endoscope 100). In this case, the position and orientation of the collector 20 are not affected by the active bent portion 102. The fixing member 23 may be attached to a distal end of the active bent portion 102 in the insertion portion 101 of the endoscope 100. In this case, the position and posture of the collector 20 follow the bending movement in the active bent portion 102.

The connecting portion 21 of the collector 20 of the present embodiment has the inner sheath 2 which is capable of advancing and retreating in the outer sheath 22 along the longitudinal axis L1 of the inner sheath 2, and the inner sheath 2 is held such that the inner sheath 2 is rotatable around the longitudinal axis L1 of the inner sheath 2 with respect to the outer sheath 22.

In the collector 20 of the present embodiment, the bag 3 of the collector 20 is positioned at the vicinity of the distal end of the insertion portion 101 of the endoscope 100. Therefore, according to the collector 20 of the present embodiment, it is easy to insert the tissue when inserting the tissue into the bag 3. Further, the position of the bag 3 with respect to the distal end of the insertion portion 101 of the endoscope 100 can be easily changed by operating the inner sheath 2, since the inner sheath 2 is capable of advancing and retracting and is rotatable with respect to the outer sheath 22.

Therefore, according to the collector 20 of the present embodiment, the bag 3 can retracted to a position not interfering with the field of view of the endoscope 100, and it is possible to move the bag 3 to a position where tissue can easily enter the bag 3 by using a grasping forceps or the like for an endoscope.

Third Embodiment

Figure 10:
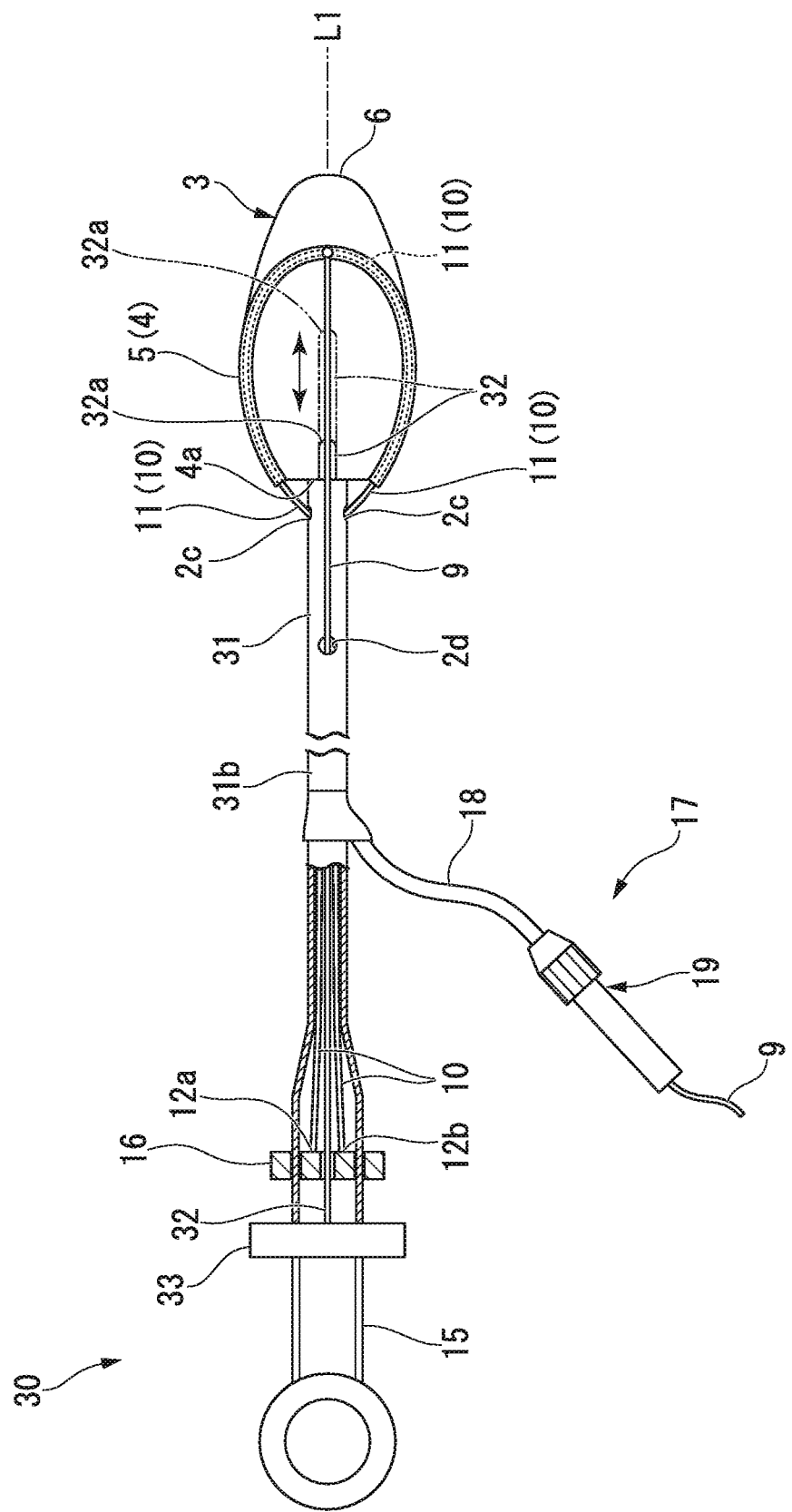
FIG. 10 is an overall view of the tissue collector of a third embodiment.
Figure 11:
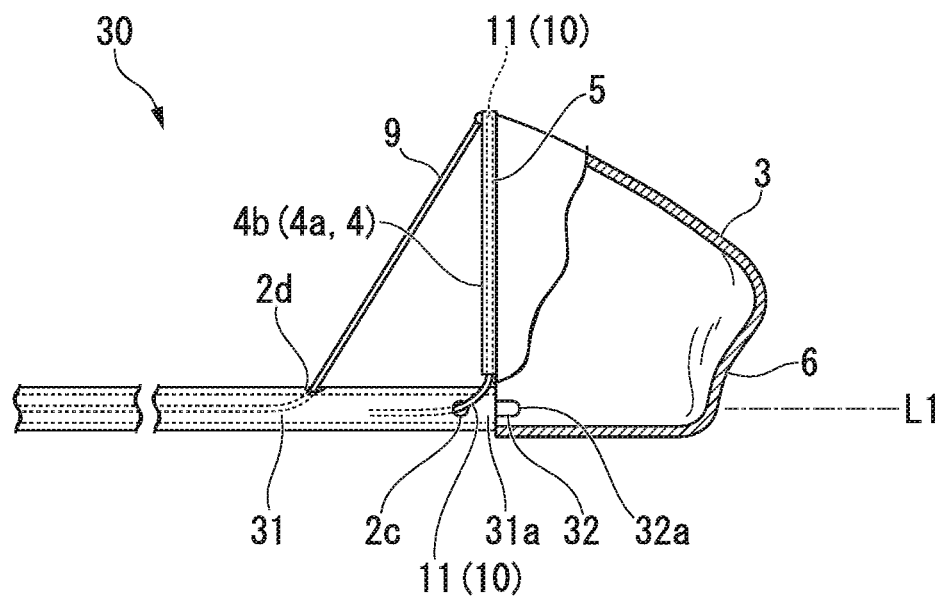
FIG. 11 is a side view showing the extending portion of the tissue collector and the bag portion.
Figure 12:
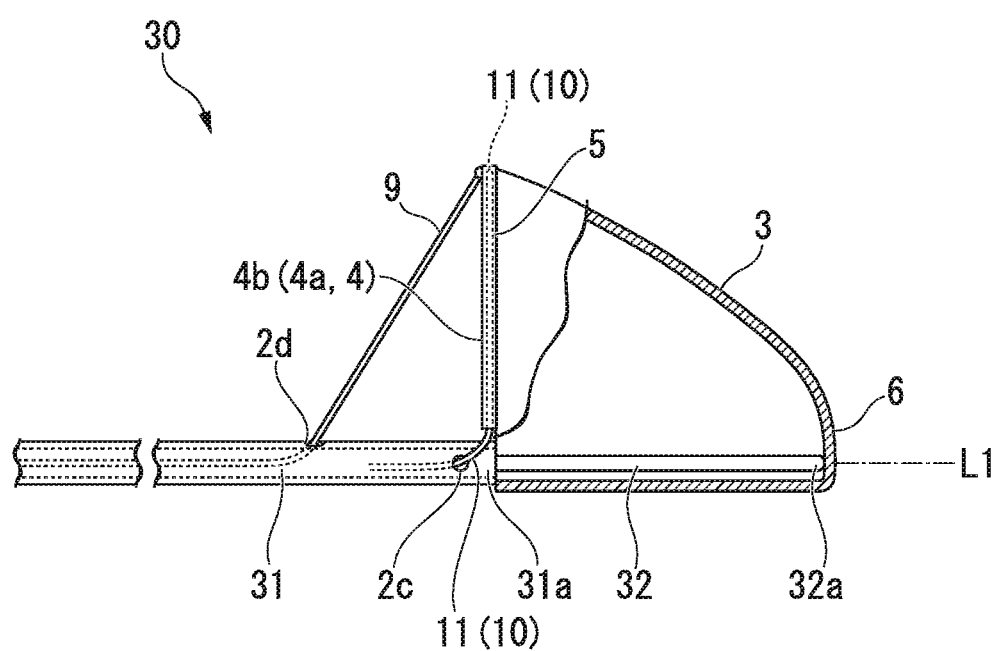
FIG. 12 is a diagram for explaining the operation of the tissue collector.

A third embodiment of the present invention will be described. FIG. 10 is an overall view of the tissue collector of the present embodiment. FIG. 11 is a side view showing the extending portion of the tissue collector and the bag portion. FIG. 12 is a diagram for explaining the operation of the tissue collector.

As shown in FIG. 10 and FIG. 11, the collector 30 of the present embodiment includes an inner sheath 31 that has a shape different from that of the inner sheath 2 disclosed in the first embodiment, an extension portion 32 that is inserted through the inner sheath 31 so as to be freely advanced and retracted in the longitudinal axis L1 direction of the inner sheath 31, and an advancing-retreating operation portion 33 for advancing and retreating the extension portion 32 in a vicinity of the base end portion 31b of the inner sheath 31. The advancing-retracting operating portion 33 of the present embodiment is attached to the operating portion main body 15 so as to be freely advancing and retracting with respect to the operating portion main body 15. The advancing-retreating operation portion 33 is arranged at a position which does not interfere with the slider 16 and the first wire 10.

As shown in FIG. 11 and FIG. 12, the extending portion 32 is capable of protruding forward from the distal end portion 31a of the inner sheath 31.

In the present embodiment, the extending portion 32 is configured to enter into the bag 3 when projecting forward from the distal end portion 31a of the inner sheath 31.

In the present embodiment, the projecting amount of the extending portion 32 from the distal end portion 31a of the inner sheath 31 can be adjusted by the advancing-retracting operation portion 33. Therefore, the size of the space for accommodating part of the tissue can be appropriately adjusted. In the present embodiment, by accommodating the extending portion 32 in the inner sheath 31 such that the distal end 32a of the extending portion 32 enters the inner sheath 31, the bag 3 can be compactly folded.

Fourth Embodiment

Figure 13:
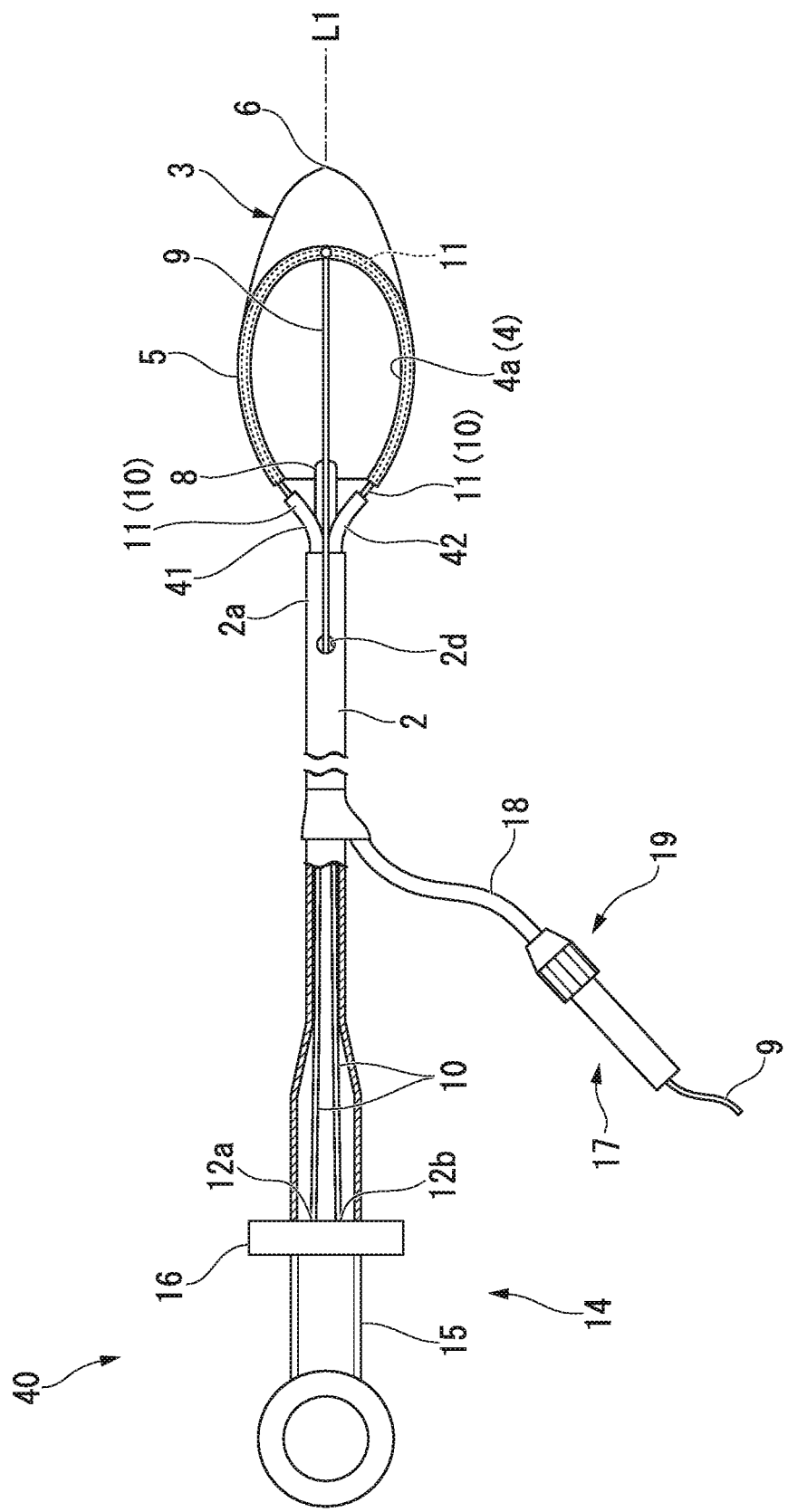
FIG. 13 is a plan view showing a vicinity of the distal end of the tissue collector of a fourth embodiment.

A fourth embodiment of the present invention will be described. FIG. 13 is a plan view showing a vicinity of the distal end of the tissue collector of the present embodiment.

As shown in FIG. 13, the collector 40 of the present embodiment has a pair of tubular portions 41, 42 that is fixed to the distal end portion 2a of the inner sheath 2 disclosed in the first embodiment.

The tubular portion 41 and the tubular portion 42 are parallel to each other on a side that is fixed to the distal end portion 2a of the inner sheath 2 and are curved so as to be separated from each other as going forward from the distal end portion 2a of the inner sheath 2. The first wire 10 is inserted into the tubular portion 41 and the tubular portion 42. The tubular portion 41 and the tubular portion 42 are made of, for example, a superelastic alloy or other shape memory alloy and are materials that maintain the above-described curved state.

In the present embodiment, the tubular portion 41 and the tubular portion 42 define a shape of the opening portion 4 of the bag 3 in a vicinity of the extending portion 8. Therefore, in the present embodiment, regardless of the raising of the bag 3, the opening portion 4 is opened in the vicinity of the extending portion 8. In this embodiment, when the wire bending portion 11 of the first wire 10 is moved forward, the wire bending portion 11 and a base end portion of the wire bending portion 11 are in a ring shape supported by the tubular portion 41 and the tubular portion 42.

As described above, according to the collector 40 of the present embodiment, the space serving as a trigger for inserting the tissue into the bag 3 is formed in the bag 3 by the tubular portion 41, the tubular portion 42, and the extension portion 8.

Fifth Embodiment

Figure 14:
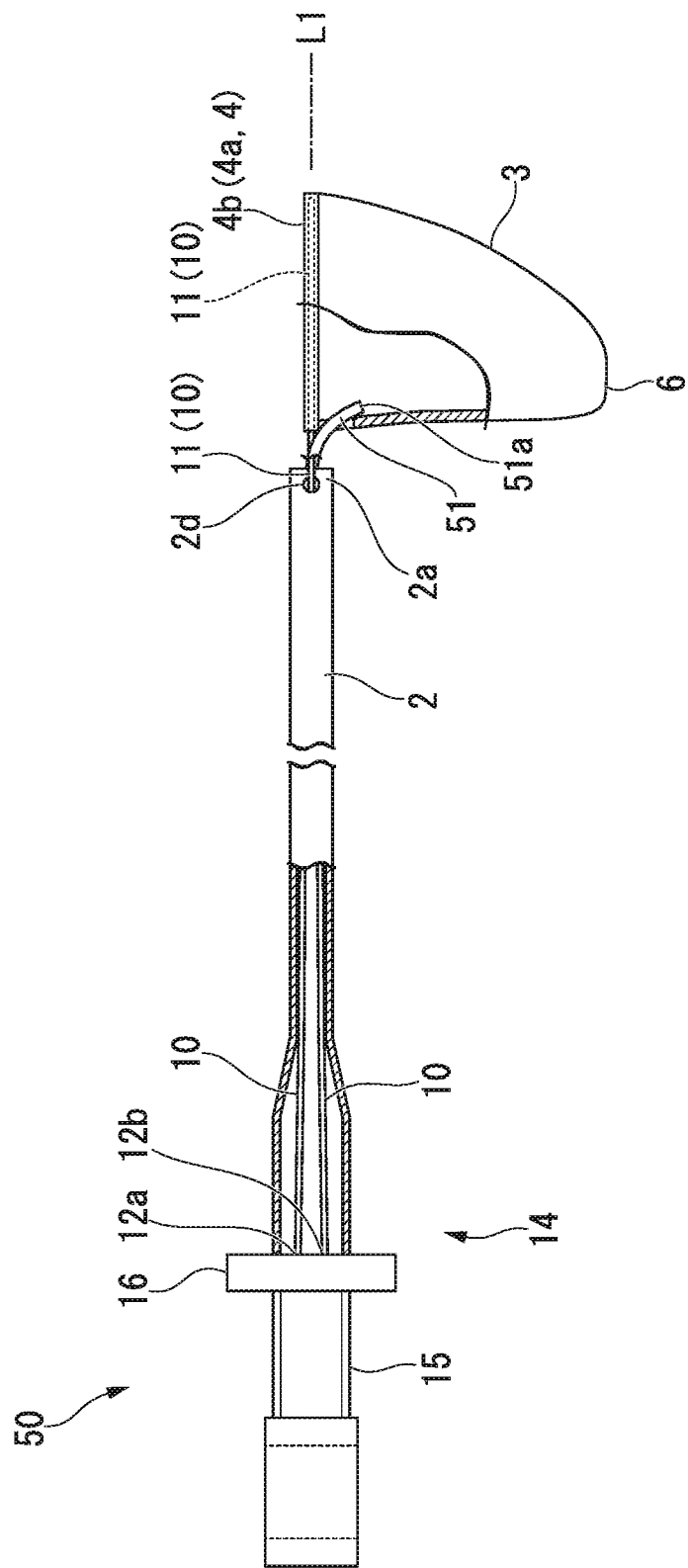
FIG. 14 is an overall view of the tissue collector of the fifth embodiment.

A fifth embodiment of the present invention will be described. FIG. 14 is an overall view of the tissue collector of the present embodiment.

As shown in FIG. 14, the collector 50 of the present embodiment is different from the collector 1 disclosed in the first embodiment in that the collector 50 does not have the thread 9 and the raising operation portion 17. That is, the collector 50 of the present embodiment is not adapted to raise the bag 3. The collector 50 of the present embodiment has the extension portion 51 that has a shape different from that of the extension portion 8 of the collector 1 disclosed in the first embodiment.

The extending portion 51 extends from the distal end portion 2a of the inner sheath 2 in an intersecting the longitudinal axis L1 direction of the inner sheath 2 and is directed to the bottom portion 6 of the bag 3.

The distal end 51a of the extending portion 51 supports the bag 3 such that the bag 3 is appropriately opened in a vicinity of the opening portion 4 by contacting with the bag 3.

In the collector 50 of the present embodiment, the extending portion 51 supports the bag 3 such that the bag 3 can be properly opened, and can prevent the bag 3 from jumping out to the opposite side through the opening portion 4.

While the preferred embodiments of the invention have been described and shown above, it should be understood that these are exemplary of the invention and are not to be considered as limiting. Additions, omissions, substitutions, and other modifications of components can be made without departing from the concept of the invention. The present invention is not limited by the description above, and it is limited by the scope of the appended claims.

For example, the bag disclosed in each of the above embodiments may have a fold formed into a tubular shape surrounding the extended portion. In this case, the extending portion is arranged inside the tubular fold line, thereby the distal end of the extending portion always comes in contact with the bag. The extension portion which is capable of advancing and retracting may be arranged inside of the tubular fold line. In this case, the fold line is able to guide the extending portion such that the distal end of the extending portion moves toward the bottom portion of the bag.

What is claimed is:

1. A tissue collector for use with an endoscope having an observation surface that observes a target, the tissue collector comprising:
    an elongated sheath having a proximal end portion and a distal end portion, the sheath extending in a direction of a longitudinal axis;
    a bag having an opening defining an opening surface and a bottom, the bag being arranged at the distal end portion, and the bag being configured to expand and contract;
    a wire protruding from the distal end portion, the wire being configured to expand the opening by moving forward from the distal end portion; and
    an extending portion arranged at the distal end portion of the sheath so as to protrude forward from the distal end portion along the longitudinal axis and enter an inside of the bag, the extending portion being configured to extend inside the bag along the bottom of the bag;
    a slider provided at a proximal end portion of the sheath; and
    a member interlocked with an operation of the slider and which varies a direction of the opening;
    wherein the member varies the direction of the opening such that the observation surface of the endoscope and the opening surface of the opening face each other.

2. The tissue collector according to claim 1, wherein
    the wire is an elastic wire extending along the opening, the elastic wire being configured to hold the opening in an annular shape, and
    the tissue collector further comprises a pair of tubes spaced from each other as going forward from the distal end portion, the pair of tubes being configured to internally hold the elastic wire such that the elastic wire is configured to be advanced and retracted.

3. The tissue collector according to claim 1, wherein the wire comprises an elastic wire having a ring shape extending from the distal end portion along the opening and returning to the distal end portion.

4. The tissue collector according to claim 1, wherein in the direction of the longitudinal axis, a distal end of the extending portion is positioned distally forward of the wire in a state where the bag is raised.

5. The tissue collector according to claim 1, wherein the bag has a fold line extending from the opening toward the bottom such that the bag is folded and unfolded by the extending portion.

6. The tissue collector according to claim 1, further comprising:
    the member has one end fixed to the opening, the member extending to the proximal end portion along the sheath, and
    the member has an other end connected to the slider.

7. The tissue collector according to claim 1, further comprising
    a connector that connects the sheath to an insertion portion of the endoscope such that the sheath extends along a longitudinal direction of the insertion portion,
    wherein the connector holds the sheath such that the sheath is configured to advance and retract along the longitudinal axis of the sheath.

8. The tissue collector according to claim 1, further comprising:
    a connector that connects the sheath to an insertion portion of the endoscope such that the sheath extends along a longitudinal direction of the insertion portion,
    wherein the connector holds the sheath such that the sheath is configured to rotate about the longitudinal axis of the sheath.

9. The tissue collector according to claim 1, wherein
    the bag has a conical shape, and
    the bottom is a tip of the conical shape.

10. The tissue collector according to claim 1, wherein the extending portion is configured to support the opening of the bag by holding a portion of the bag contacting the extending portion when the bag is raised with respect to the sheath, and is configured to form a space for accommodating a tissue disposed into the bag.

11. The tissue collector according to claim 1, wherein the member is a thread fixed to the opening.

12. The tissue collector according to claim 1, wherein the extending portion is an elongated member disposed in the sheath.

13. A tissue collector system comprising:
    the tissue collector according to claim 1; and
    the endoscope attached along the longitudinal axis on an outer peripheral surface of the sheath, the observation surface being provided in a distal end surface of the endoscope.

* * * * *